United States Patent [19]
Weber et al.

[11] 4,199,588
[45] Apr. 22, 1980

[54] 6-PHENYL-4H-S-TRIAZOLO-[3,4C]-THIENO-[2,3E]-1,4-DIAZEPINES AND SALTS THEREOF

[75] Inventors: Karl-Heinz Weber, Gau-Algesheim; Adolf Bauer, Ingelheim am Rhein; Peter Danneberg, Ockenheim; Franz J. Kuhn, Bingen, all of Fed. Rep. of Germany

[73] Assignee: Boehringer Ingelheim GmbH, Ingelheim am Rhein, Fed. Rep. of Germany

[21] Appl. No.: 855,753

[22] Filed: Nov. 30, 1977

Related U.S. Application Data

[63] Continuation of Ser. No. 672,281, Mar. 31, 1976, abandoned, which is a continuation-in-part of Ser. No. 554,309, Feb. 28, 1975, abandoned.

[30] Foreign Application Priority Data

| Mar. 2, 1974 [DE] | Fed. Rep. of Germany | 2410030 |
| Jul. 20, 1974 [DE] | Fed. Rep. of Germany | 2435041 |
| Sep. 24, 1974 [DE] | Fed. Rep. of Germany | 2445430 |
| Dec. 21, 1974 [DE] | Fed. Rep. of Germany | 2460776 |

[51] Int. Cl.² .................. A61K 31/55; C07D 495/14
[52] U.S. Cl. ...................... 424/267; 260/239.3 B; 260/244.4; 549/68; 260/330.3; 260/245.5; 424/232; 424/253; 424/263; 424/269
[58] Field of Search ........ 260/308 R, 293.57, 294.8 B, 260/244.4; 424/269, 263, 267

[56] References Cited

U.S. PATENT DOCUMENTS

| Re. 28,505 | 5/1975 | Hester | 260/308 R |
| 3,709,899 | 1/1973 | Hester | 260/308 R |
| 3,751,426 | 8/1973 | Hester | 260/308 R |
| 3,849,934 | 11/1974 | Coffen et al. | 260/308 R |
| 3,856,802 | 12/1974 | Szmuszkovicz | 260/308 R |
| 3,904,641 | 9/1975 | Nakanishi et al. | 260/308 R |
| 4,094,984 | 6/1978 | Weber et al. | 260/308 R |

FOREIGN PATENT DOCUMENTS 2228044  12/1972  Fed. Rep. of Germany ...... 260/308 R
2405682  8/1974  Fed. Rep. of Germany ...... 260/308 R

OTHER PUBLICATIONS

Allgeier et al., Chem. Abstracts, vol. 77, Abstract No. 88554g (1972).

Primary Examiner—Alton D. Rollins
Attorney, Agent, or Firm—Hammond & Littell, Weissenberger & Muserlian

[57] ABSTRACT

Compounds of the formula wherein
  $R_1$ is hydrogen, chlorine, bromine or alkyl of 1 to 4 carbon atoms;
  $R_2$ is hydrogen, fluorine, chlorine, bromine, nitro or trifluoromethyl; and
  $R_3$ is chlorine, bromine, alkoxy of 1 to 3 carbon atoms, alkylmercapto of 1 to 3 carbon atoms, cycloalkyl of 3 to 6 carbon atoms, cycloalkenyl of 3 to 6 carbon atoms, or a saturated or unsaturated 5- to 6-membered heterocycle comprising an oxygen, sulfur or nitrogen heteroatom, where a substitutable nitrogen heteroatom may optionally have a lower akyl substituent attached thereto;

and non-toxic, pharmacologically acceptable acid addition salts thereof; the compounds as well as their salts are useful as tranquilizers, muscle-relaxants and anticonvulsants.

12 Claims, No Drawings

6-PHENYL-4H-S-TRIAZOLO-[3,4C]-THIENO-[2,3E]-1,4-DIAZEPINES AND SALTS THEREOF

This is a continuation of copending application Ser. No. 672,281 filed Mar. 3, 1976, now abandoned; which in turn is a continuation-in-part of copending application Ser. No. 554,309 filed Feb. 28, 1975, now abandoned.

This invention relates to novel 6-phenyl-4H-s-triazolo-[3,4c]-thieno-[2,3e]-1,4-diazepines and non-toxic acid addition salts thereof, as well as to methods of preparing these compounds.

More particularly, the present application relates to a novel class of compounds represented by the formula

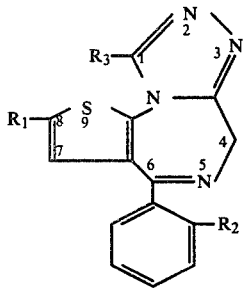

wherein
$R_1$ is hydrogen, chlorine, bromine or alkyl of 1 to 4 carbon atoms;
$R_2$ is hydrogen, fluorine, chlorine, bromine, nitro or trifluoromethyl; and
$R_3$ is chlorine, bromine, alkoxy of 1 to 3 carbon atoms, alkylmercapto of 1 to 3 carbon atoms, cycloalkyl of 3 to 6 carbon atoms, cycloalkenyl of 3 to 6 carbon atoms, or a saturated or unsaturated 5- to 6-membered heterocycle comprising an oxygen, sulfur or nitrogen heteroatom, where a substitutable nitrogen nitrogen heteroatom may optionally have a lower alkyl substituent attached thereto;
and non-toxic, pharmacologically acceptable acid addition salts thereof.

The compounds embraced by formula I above may be prepared by the following methods:

Method A

For the preparation of a compound of the formula I wherein $R_1$ and $R_2$ have the meanings defined above and $R_3$ has the meanings defined above except chlorine and bromine, (a) by reacting a compound of the formula

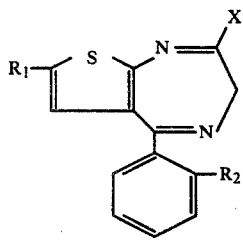

wherein $R_1$ and $R_2$ have the meanings previously defined and X is SH—, NH$_2$—, lower alkoxy, lower alkylmercapto- or halogen, with a compound of the formula

R$_3$'CO—NH—NH$_2$ (III)

wherein $R_3'$ has the meanings of $R_3$ except chlorine and bromine; or (b) by reacting a compound of the formula

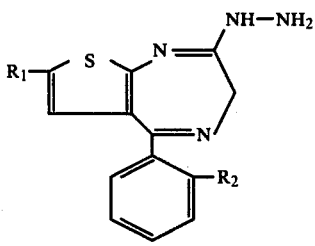

wherein $R_1$ and $R_2$ have the meanings previously defined, with an acid of the formula

R$_3'$—COOH (V)

wherein $R_3'$ has the meanings defined above, or with a functional derivative of this acid.

Method B

For the preparation of a compound of the formula I wherein $R_1$ and $R_2$ have the meanings previously defined and $R_3$ is chlorine, bromine, alkoxy of 1 to 3 carbon atoms or alkylmercapto of 1 to 3 carbon atoms, by chlorinating or brominating a compound of the formula

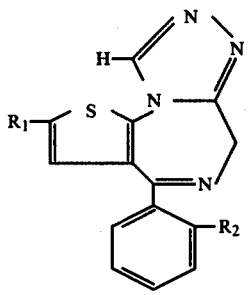

wherein $R_1$ and $R_2$ have the meanings previously defined and, if desired, subsequently exchanging the chlorine or bromine substituent in the 1-position for an alkoxy or alkylmercapto substituent.

The reaction described under method A (a) may be carried out at temperatures between 100° and 250° C. without a solvent as well as with a solvent, such as methanol, ethanol, dioxane, chloroform, tetrahydrofuran, benzene, toluene, xylene or mixtures of any two or more of these, and in the presence or absence of an acid catalyst, such as hydrochloric acid, sulfuric acid, phosphoric acid, polyphosphoric acid, acetic acid, propionic acid, benzenesulfonic acid or toluenesulfonic acid; it is generally allowed to proceed to the end product without isolating the intermediate product of the formula

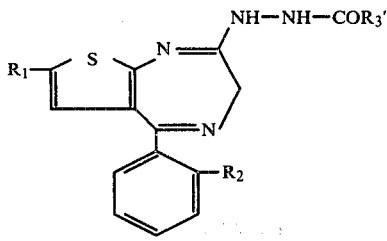

wherein $R_1$, $R_2$ and $R_3'$ have the meanings previously defined, but under milder reaction conditions (e.g. at room temperature) it is possible to isolate the intermediate product without difficulties.

The reaction described under method A (b) proceeds with the free acid of the formula V or with a suitable functional derivative of this acid. Examples of suitable functional derivatives of the acid of the formula V are an orthoester of the formula $R_3'$—$C(OR')_3$; an iminoether of the formula $R_3'$—$C(=NH)$—$OR'$; an amidine of the formula $R_3'$—$C$—$(=NH)$—$NH_2$; an amide of the formula $R_3'$—$CONH_2$; a thioamide of the formula $R_3'$—$CSNH_2$; an ester of the formula $R_3'$—$COOR''$ (for example, a methyl, ethyl or nitrophenyl ester); an acid anhydride of the formula $(R_3'$—$CO)_2O$; an acid halide of the formula $R_3'$—$COHal$; or a nitrile of the formula $R_3'$—$CN$; in these formulas $R_3'$ has the meanings previously defined, $R'$ is lower alkyl, and $R''$ is aliphatic, araliphatic or aromatic hydrocarbyl. The iminoethers and amidines are used in the form of their salts formed with mineral acids, e.g. as their chlorohydrates, as conventional.

The reaction conditions may be chosen pursuant to the particular acid derivative which is used. Generally, the reaction may be carried out without a solvent or with a solvent, such as in methanol, ethanol, chloroform, tetrahydrofuran, benzene, toluene or mixtures of any two or more of these, without or in the presence of an acid catalyst, such as hydrochloric acid, sulfuric acid, phosphoric acid, polyphosphoric acid, acetic acid, propionic acid, benzenesulfonic acid or toluenesulfonic acid. The presence of a base, such as 2-methylimidazole, as catalyst is useful as well. The reaction temperature lies between 0° and 300° C., preferably 20° to 180° C.

The following further describe the particular variants of this method:

Variant I

In this case the functional derivative of the acid of the formula V is an orthoester of the formula $R_3'$—$C(OR')_3$ where $R_3'$ and $R'$ have the meanings defined above. Usually, the reaction proceeds in the presence of an excess of the orthoester which serves simultaneously as the solvent medium, at temperatures between 90° and 100° C.; or one of the aforementioned solvents, optionally in the presence of one of the aforementioned catalysts, at temperatures between room temperature and the reflux temperature of the reaction mixture.

Variant II

In this case the functional derivative of the acid of the formula V is an iminoether of the formula $R_3'$—$C(=NH)$—$OR'$, where $R_3'$ and $R'$ have the previously defined meanings. It is advantageous to perform the reaction in one of the previously mentioned solvents at a temperature between room temperature and the reflux temperature of the reaction mixture.

Variant III

In this case the functional derivative of acid of the formula V is an amidine of the formula $R_3'$—$C(=NH)$—$NH_2$, where $R_3'$ has the meaning previously defined. It is advantageous to perform reaction in the presence of a basic catalyst, such as 2-methylimidazole, at elevated temperatures, for example between 150° and 250° C. In case the reaction temperature is lower, for example if the reaction is carried out at room temperature, an intermediate product of the formula

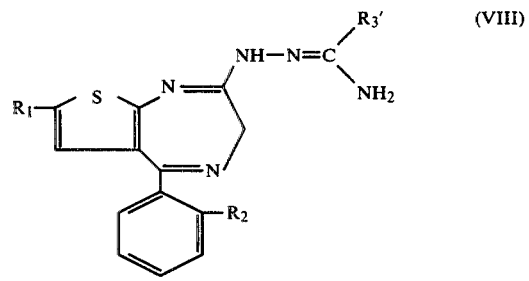

where $R_1$, $R_2$ and $R_3'$ have the previously defined meanings, is first formed. This intermediate product may be isolated and subsequently subjected to a cyclization reaction by heating it at 150° to 250° C. However, isolation is not required by any means.

Variant IV

In this case the functional derivative of the acid of the formula V is an amide or thioamide of the formula $R_3'$—$CONH_2$ or $R_3'$—$CSNH_2$, where $R_3'$ has the meanings defined above. The reaction may be performed with or without a solvent, and without or with catalyst, at temperatures between 0° and 300° C.

Variant V

Here the functional derivative of acid of the formula V is an ester of the formula $R_3'$—$COOR''$, an anhydride of the formula $(R_3'CO)_2O$, an acid halide of the formula $R_3'$—$COCl$, or a nitrile of the formula $R_3'$—$CN$, where $R_3'$ and $R''$ have the previously defined meanings. At first, the intermediate product of the formula VII is formed, which is then cyclized as indicated under method A(a).

For the preparation of those end products of the formula I, wherein $R_3$ is chlorine, bromine, alkoxy of 1 to 3 carbon atoms or alkylmercapto of 1 to 3 carbon atoms, pursuant to method B, a compound of the formula VI is brominated or chlorinated. The halogenation is effected in a solvent, such as carbon tetrachloride, chloroform, methylenechloride, dioxane, tetrahydrofuran, dimethylformamide or a suitable hydrocarbon, optionally in the presence of a tertiary organic base, such as pyridine, or else by means of a halosuccinimide. The temperature of the reaction mixture, depending upon the starting material used and the method applied, lies between room temperature and the reflux temperature of the reaction mixture.

If desired, an 8-halo-substituted compound thus obtained may be converted into the corresponding alkoxy or alkylmercapto compound.

In case an alkoxy group is introduced, the halogenated compound is dissolved in an alkalimetal alcoholate, and the solution is refluxed.

For the preparation of an alkylmercapto compound, the halogenated compound is dissolved in an aprotic solvent, such as dioxane, tetrahydrofuran, dimethylformamide or hexamethylphosphorus triamide (HMPT) or an alcohol, and reacted with an alkalimetal mercaptide; for this reaction the alkali mercaptide may also be made in situ, for instance by introducing a mercaptan into the solution of the halogenated compound containing an alkalimetal alcoholate.

The end products of the formula I, except those which are substituted in the 1-position of the molecule by a 5- to 6-membered, saturated or unsaturated, sulfur-containing heterocycle, form acid addition salts with inorganic or organic acids. Examples of non-toxic, pharmacologically acceptable acid addition salts are those formed with hydrohalic acids, sulfuric acid, phosphoric acid, nitric acid, cyclohexylsulfaminic acid, citric acid, tartaric acid, ascorbic acid, maleic acid, formic acid, salicyclic acid, methane- or toluene-sulfonic acid, 8-chlorotheophylline or the like.

The starting compounds of the formulas III and V are described in the literature, and the preparation of the compounds of the formulas VI, VII and VIII is described above.

The hydrazine derivatives of the formula IV may be prepared by reacting a compound of the formula II with hydrazine. This reaction may be performed in one of the abovementioned solvents and, if desired, in the presence of one of the previously mentioned acid catalysts, advantageously at a temperature between room temperature and the reflux temperature of the reaction mixture.

The compounds of the formula II wherein $R_1$ is halogen, which may be reacted either directly with compounds of the formula III to form compounds of the formula I, or else may be reacted with hydrazine to form compounds of the formula IV, are prepared starting from known (see German Offenlegungsschrift No. 2,217,157) compounds of the formula

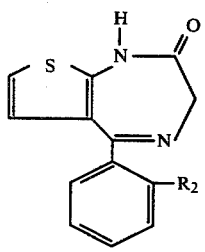

(IX)

wherein $R_2$ has the previously defined meanings, by halogenating them in conventional manner, and reacting the resulting compounds of the formula

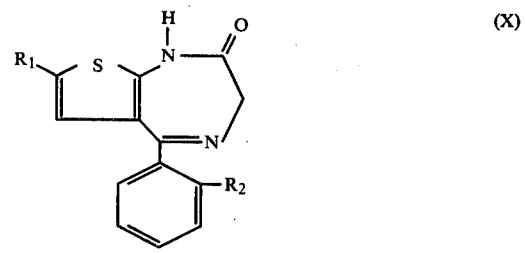

(X)

wherein $R_1$ and $R_2$ have the previously defined meanings (some of which are also known from German Offenlegungsschrift No. 2,221,623), in a solvent, such as pyridine, dimethylformamide or tetrahydrofuran or mixtures thereof. The reaction temperature may lie between room temperature and the reflux temperature of the reaction mixture. In this manner the compounds of the formula II wherein X is —SH are obtained. They exist in tautomeric equilibrium with the corresponding thiono compounds, as follows:

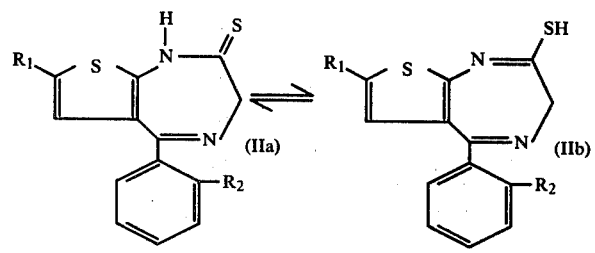

wherein $R_1$ and $R_2$ have the previously defined meanings. These compounds may, after they have been converted into the corresponding salts by reaction with a metallizing agent, such as sodium methylate or sodium amide in a solvent, be reacted without previous isolation with alkylating agents, such as methyl iodide or another lower alkyl iodide to form those compounds of the formula II wherein X is lower alkylthio.

Compounds of the formulas IX and X may be obtained pursuant to the methods of German Offenlegungsschrift Nos. 2,107,356 and 2,144,105 namely by subjecting compounds of the formula

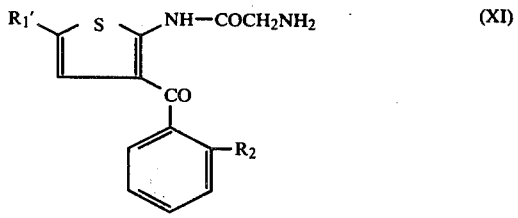

(XI)

wherein $R^2$ has the previously defined meanings and $R_1'$ is hydrogen or bromine, to intramolecular condensation. An especially advantageous variant of this reaction consists of effecting the cyclization by boiling in toluene in a vessel provided with a water trap, using silicagel as the dehydrating agent. In this manner significantly higher yields and purer products are obtained.

Compounds of the formula II, wherein X is lower alkoxy, may be obtained by reacting known aminoketones of the formula

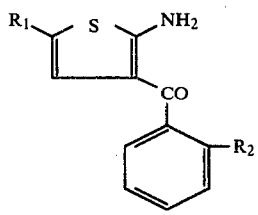

wherein $R_1$ and $R_2$ have the previously defined meanings, with a halo-orthoacetate of the formula

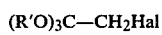

(XIII)

wherein R' has the previously defined meanings and Hal is chlorine, bromine or iodine, to form a compound of the formula

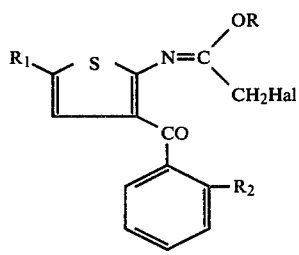

(XIV)

wherein R, $R_1$, $R_2$ and Hal have the previously defined meanings. In those instances where Hal is chlorine, it is advantageous first to exchange the aliphatically bonded chlorine atom in the compound of the formula XIV for iodine by means of the Finkelstein Reaction, for example by reacting it with sodium iodide in acetone. Then, the iodo-substituted compound thus obtained is reacted with ammonia in dioxane or tetrahydrofuran. In this manner, an intermediate amino compound of the formula

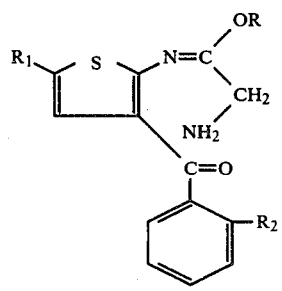

(XV)

wherein R, $R_1$ and $R_2$ have the previously defined meanings, is formed which, however, cyclizes spontaneously into a compound of the formula

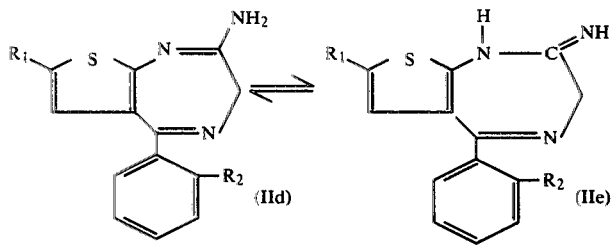

(IIc)

wherein R, $R_1$ and $R_2$ have the previously defined meanings.

Compounds of the formula II, wherein X is amino, may be prepared by reacting compounds of the formula X, which were obtained by halogenation of compounds of the formula IX, with ammonia. The reaction is advantageously performed in a solvent, such as tetrahydrofuran, and in the presence of a Lewis acid, such as titanium chloride, for example.

These compounds also exist in tautomeric equilibrium as follows:

wherein $R_1$ and $R_2$ have the previously defined meanings.

The following examples illustrate the present invention and will enable others skilled in the art to understand it more completely. It should be understood, however, that the invention is not limited solely to the particular examples given below.

EXAMPLE 1

1,8-Dibromo-6-(o-chloro-phenyl)-4H-s-triazolo-[3,4c]-thieno-[2,3e]-1,4-diazepine (a) 10 gm of 8-bromo-6-(o-chloro-phenyl)-4H-s-triazolo-[3,4c]-thieno-[2,3e]-1,4-diazepine were dissolved in a mixture of 20 ml of pyridine and 100 ml of methylenechloride, and the solution was heated for 7 hours. Thereafter, a solution of 6.3 gm of bromine in 25 ml of methylenechloride was added within 5 minutes, and the mixture was refluxed for another 3 hours. Subsequently, the reaction mixture was cooled, diluted with methylene chloride and extracted twice with 1 N hydrochloric acid and once with water. After drying, the methylene chloride phase was evaporated, and the residue recrystallized from ethanol. 7.0 gm (60% of theory) of the compound named in the heading, m.p. 210°–211° C., were obtained.

(b) The starting compound was obtained as follows:
27 gm of 7-bromo-5-(o-chloro-phenyl)-2-hydrazino-3H-[2,3e]-thieno-1,4-diazepine, m.p. ~300° C. (decomp.), were refluxed in a mixture of 23 ml of orthoformate and 300 ml of ethanol for 30 minutes. The solvent was evaporated, and the residue was triturated with ether. Yield: 26 gm; m.p. 214°–216° C.

EXAMPLE 2

8-Bromo-6-(o-chloro-phenyl)-1-methoxy-4-H-s-triazolo-[3,4c]-thieno-[2,3e]-1,4-diazepine 12 gm of 1,8-dibromo-6-(o-chloro-phenyl)-4H-s-triazolo-[3,4c]-thieno-[2,3e]-1,4-diazepine were refluxed in a solution of 0.6 gm of sodium in 70 ml of methanol for 2 hours. Subsequently, the reaction mixture was evaporated, and the residue was diluted with water and repeatedly extracted with methylene chloride. The methylene chloride phase was dried, the methylene chloride evaporated, and the residue was recrystallized from ethanol, yielding 7 gm (76% of theory) of the compound named in the heading, m.p. 198°-200° C.

EXAMPLE 3

8-Bromo-6-(o-chloro-phenyl)-1-methylmercapto-4H-s-triazolo-[3,4c]-thieno-[2,3e]-1,4-diazepine 0.15 gm of sodium was dissolved in 40 ml of absolute methanol, and 340 mgm of methylmercaptan were introduced into the solution. Then, the solution was admixed with 2.5 gm of 1,8-dibromo-6-(o-chloro-phenyl)-4H-s-triazolo-[3,4c]-thieno-[2,3e]-1,4-diazepine, and the mixture was heated to between 40° and 50° C. After about 30 minutes no more dibromo compound could be detected by thin-layer chromatography. Then, the solution was evaporated, the residue was taken up in methylene chloride, the methylene chloride solution was extracted with water several times, the organic phase dried, the solvent was evaporated, and the residue was chromatographed on a $SiO_2$-column. 920 mgm (40% of theory) of the compound named in the heading, m.p. 158°-160° C., were obtained.

EXAMPLE 4

8-Bromo-6-(o-chloro-phenyl)-1-cyclohexyl-4H-s-triazolo-[3,4c]-thieno-[2,3e]-1,4-diazepine (a) 3.7 gm of 7-bromo-5-(o-chloro-phenyl)-3H-[2,3e]-thieno-1,4-diazepine-2-thione were dissolved in 40 ml of dioxane, and the solution was refluxed with 4 gm of cyclohexane-carboxylic acid hydrazide for 30 minutes. After evaporation of the solvent, the crystalline residue was treated with ether; 4.8 gm of 7-bromo-5-(o-chloro-phenyl)-2-(cyclohexylcarbonyl-hydrazino)-3H-[2,3e]-thieno-1,4-diazepine, m.p. 140° C. (decomp.), were obtained.

(b) A mixture of 4.8 gm of hydrazino compound thus obtained with 150 ml of toluene and 25 gm of $SiO_2$ was heated at the boiling point for 3 hours in a vessel equipped with a water trap. Subsequently, the insoluble matter was removed by suction filtration, and the reaction product was eluted with methanol from silicagel. 1.6 gm (35% of theory) of the compound named in the heading, m.p. 179°-180° C., were obtained.

EXAMPLE 5

1-Ethoxy-8-bromo-6-(o-chloro-phenyl)-4H-s-triazolo-[3,4c]-thieno-[2,3e]-1,4-diazepine A mixture of 3.7 gm of 7-bromo-5-(o-chloro-phenyl)-3H-[2,3e]-thieno-1,4-diazepine-2-thione, 60 ml of n-butanol and 1 gm of ethyl hydrazine-carboxylate was refluxed for 30 minutes. Upon cooling, 2 gm of the corresponding hydrazide, m.p. 236° C., precipitated out. The crystals were collected by suction filtration and boiled for 3 hours with 100 ml of xylene and 20 gm of $SiO_2$ in a vessel equipped with a water trap. Then, the insoluble matter was separated by suction filtration, and the compound named in the heading was eluted with methanol from the silicagel. 0.7 gm (37% of theory) of the desired product, m.p. 144°-146° C., was obtained.

EXAMPLE 6

8-Bromo-6-(o-chloro-phenyl)-1-tetrahydrofuranyl-(2)-4H-s-triazolo-[3,4c]-thieno-[2,3e]-1,4-diazepine (a) 3.7 gm (0.01 mol) of 7-bromo-5-(o-chloro-phenyl)-3H-[2,3e]-thieno-1,4-diazepine-2-thione, m.p. 214° C. (decomp.), were refluxed with 50 ml of dioxane and 1.3 gm of tetrahydrofuran-2-carboxylic acid hydrazide for 2 hours. Thin-layer chromatography of a sample showed that after this time the 7-bromo-5-(o-chloro-phenyl)-2-tetrahydrofuranyl-(2)-carbonylhydrazino-3H-[2,3e]-thieno-1,4-diazepine intermediate product which had formed under the indicated reaction conditions had already cyclized into the compound named in the heading. The solvent was evaporated, and the residue was chromatographed on $SiO_2$, using methylene chloride containing 2% methanol as the eluant. After recrystallization from ethanol, 3.1 gm (66.2% of theory) of the desired compound, m.p. 138°-140° C., were obtained.

(b) 3.7 gm (0.01 mol) of 7-bromo-5-(o-chloro-phenyl)-3H-[2,3e]-thieno-1,4-diazepine-2-thione were refluxed in 50 ml of tetrahydrofuran with 1.3 gm of tetrahydrofuran-2-carboxylic acid hydrazide for 3 hours. A dark red solution was obtained. After evaporation of the solvent, the residue was caused to crystallize with a little ethanol, and the crystals were collected by suction filtration and washed with ether. In this manner 2.8 gm (59.7% of theory) of 7-bromo-5-(o-chloro-phenyl)-2-tetrahydrofuranyl-(2)-carbonylhydrazino-3H-[2,3e]-thieno-1,4-diazepine, m.p. 199°-200° C., were obtained. This compound was heated with 20 gm of silicagel in 60 ml of xylene for 2 hours in a vessel equipped with a water trap. The xylene was decanted, and the desired compound was extracted from silicagel several times with boiling methanol. The eluate was evaporated, and the residue was recrystallized from ethanol, yielding 2.0 gm (74.7% of theory) of the compound named in the handling, m.p. 140°-142° C. The 7-bromo-5-(o-chloro-phenyl)-3H-[2,3e]-thieno-1,4-diazepine-2-thione used as the starting compound was obtained by heating the known compound 7-bromo-5-(o-chloro-phenyl)-3H-[2,3e]-thieno-1,4-diazepin-2-one with phosphorus pentasulfide in pyridine.

EXAMPLE 7

8-Bromo-6-(o-chloro-phenyl)-1-tetrahydropyranyl-(2)-4H-s-triazolo[3,4c]-thieno-[2,3e]-1,4-diazepine 3.7 gm (0.01 mol) of 7-bromo-5-(o-chloro-phenyl)-3H-[2,3e]-thieno-1,4-diazepine-2-thione were refluxed with 80 ml of ethanol, 8 ml of pyridine and 1.5 gm of tetrahydropyrane-2-carboxylic acid hydrazide for 3 hours. Afterwards, the solvent was evaporated, and the residue was triturated with cold ethanol. 3.5 gm of 7-bromo-5-(o-chloro-phenyl)-2-tetrahydropyranyl-(2)-carbonylhydrazino-3H-[2,3e]-thieno-1,4-diazepine, m.p. 185° C., were obtained. This compound was heated in 60 ml of xylene with 20 gm of silicagel for 2 hours in a vessel equipped with a water trap. The xylene was then decanted, and the desired compound was eluted from silicagel with boiling methanol. The eluate was evaporated, and the residue was recrystallized from ethanol, yielding 1.9 gm of the compound named in the heading, m.p. 211°-212° C.

EXAMPLE 8

8-Bromo-6-(o-chloro-phenyl)-1-[tetrahydropyranyl-(4)]-4H-s-triazolo[3,4c]-thieno-[2,3e]-1,4-diazepine 3.7 gm (0.01 mol) of 7-bromo-5-(o-chloro-phenyl)-3H)-[2,3e]-thieno-1,4-diazepine-2-thione were suspended in 50 ml of tetrahydrofuran, and the suspension was admixed in small portions with 0.5 gm of a 50% sodium hydride dispersion. The temperature was kept at 20°-25° C. by cooling on ice. After 15 minutes, 1 ml of methyl iodide was added, and the mixture was stirred for 30 minutes at 40° C. The solvent was then evaporated, and the residue was taken up in methylene chloride. The inorganic salts were washed out with water. After evaporation of the solvent, the raw methylmercapto compound was obtained.

3.2 gm of this methylmercapto compound were refluxed for 3 hours with 1.2 gm of tetrahydropyranyl-4-carboxylic acid hydrazide in 50 ml of methanol while passing nitrogen through the solution. Then the solvent was evaporated, and the residue was admixed with 100 ml of xylene and 30 gm of silicagel. For completion of the cyclization reaction, the mixture was heated for 3 hours in a vessel equipped with a water trap. Subsequently, the reaction mixture was worked up as described in Example 1(b). After recrystallization from dioxane 3.4 gm (73% of theory) of the colorless crystalline compound named in the heading, m.p. 257°-258° C. were obtained.

EXAMPLE 9

8-Chloro-6-(o-chloro-phenyl)-1-[tetrahydrofuranyl-(2)]-4H-s-triazolo-[3,4c]-thieno-[2,3e]-diazepine 3.25 gm (0.01 mol) of 7-chloro-5-(o-chloro-phenyl)-2-hydrazino-3H[2,3e]-thieno-1,4-diazepine, m.p. 236° C. (decomp.), prepared by reacting the corresponding thienodiazepinethione with hydrazine, were suspended in 100 ml of tetrahydrofuran, and the suspension was admixed with 1.0 ml of tetrahydrofuran-2-carboxylic acid chloride. The mixture was refluxed for 5 hours, the solvent was then evaporated, and the residue was worked up as described in Example 1(a), yielding 1.3 gm (32% of theory) of the colorless crystalline compound named in the heading, m.p. 191° C.

EXAMPLE 10

8-Bromo-6-(o-chloro-phenyl)-1-[N-methyl-piperidyl-(3)]-4H-s-triazolo-[3,4c]-thieno-[2,3e]-1,4-diazepine and its hydrochloride (a) 37.1 gm (0.1 mol) of 7-bromo-5-(o-chloro-phenyl)-3H-[2,3e]-thieno-1,4-diazepine-2-thione were dissolved or suspended in 300 ml of tetrahydrofuran, and the mixture was refluxed with 16 gm of N-methyl-piperidyl-3-carboxylic acid hydrazide, m.p. 83°-85° C. (prepared from the corresponding ester with hydrazine) for 4 hours, while passing nitrogen continuously through the solution. After evaporation of the solvent, the residue was taken up in methylene chloride, the solution was washed with water, the solvent was evaporated, and the residue was caused to crystallize with ether. 42 gm (86% of theory) of 7-bromo-5-(o-chloro-phenyl)-2-[N-methylpiperidyl-(3)]-carbonylhydrazino-3H-[2,3e]-thieno-1,4-diazepine, m.p. 208°-209° C. (decomp.), were obtained.

(b) 42 gm of this compound were suspended in 1400 ml of xylene, and the suspension was admixed with 100 gm of silicagel while stirring at a temperature of 100°-120° C. After heating it in a vessel equipped with a water trap for one hour, the reaction mixture was cooled, the solvent was removed by suction filtration, and the desired compound was eluted from the silicagel with warm methanol. 16 gm of the colorless crystalline base named in the heading, m.p. 240°-241° C., were obtained.

(c) 10 gm of the base were suspended in 20 ml of ethanol, and the solution was admixed slowly with 20 ml of ethanolic hydrochloric acid, whereby a solution was first formed and then the hydrochloride crystallized out. It was recrystallized from ethanol in the presence of charcoal, whereupon it had a m.p. of 257°-258° C. (decomp.).

Using the above-described methods, the following additional compounds of the formula I were prepared:

| Example No. | $R_1$ | $R_2$ | $R_3$ | M.P. °C. | M.P. of corresponding hydrazide of the formula VII, °C. |
|---|---|---|---|---|---|
| 11 | Br | Cl | ◁ | 212-213 | 236 (decomp.) |
| 12 | Br | Cl | Cl | 161-162 | — |
| 13 | Br | Cl | ⬠ | 190-191 | 110 (decomp.) |
| 14 | Br | Cl | ◇ | 192-193 | oil |
| 15 | Cl | Cl | Br | 170-172 | — |
| 16 | Cl | Cl | OCH$_3$ | 160-162 | — |
| 17 | Cl | Cl | ⬡H | 188-189 | 177 (decomp.) |

-continued

| Example No. | $R_1$ | $R_2$ | $R_3$ | M.P. °C. | M.P. of corresponding hydrazide of the formula VII, °C. |
|---|---|---|---|---|---|
| 18 | $C_2H_5$ | Cl | cyclohexyl (H) | 128–129 | 203 |
| 19 | H | H | cyclohexyl (H) | 173–180 | oil |
| 20 | H | Cl | Br | 202–203 | — |
| 21 | H | Cl | $OCH_3$ | 184–185 | — |
| 22 | $C_2H_5$ | Cl | Br | 175–176 | — |
| 23 | $C_2H_5$ | Cl | $OCH_3$ | oil | — |
| 24 | H | H | $OCH_3$ | 167–168 | — |
| 25 | H | H | Br | 197–199 | — |
| 26 | Br | Cl | cyclohexenyl | 145–147 | — |
| 27 | Br | Cl | tetrahydrofuryl | 190–191 | 212 (decomp.) |
| 28 | Br | Cl | tetrahydropyranyl | 187–188 | 200 (decomp.) |
| 29 | H | H | tetrahydrofuryl | 138–140 (1 mol $CH_3OH$) | — |
| 30 | Br | Br | tetrahydropyranyl | 242 | — |
| 31 | $C_2H_5$ | Cl | tetrahydropyranyl | 174–175 | 197 (decomp.) |
| 32 | Br | Cl | N-methylpiperidyl ($CH_3$) | 171–180 | 217–218 (decomp.) |
| 33 | Br | Cl | pyridyl (N) | 260–262 | 217 (decomp.) |
| 34 | Br | Cl | piperidyl (HN) | 251–253 | 196 (decomp.) |
| 35 | Br | Cl | pyrrolidinyl (HN) | 223–225 | 215–220 (decomp.) |
| 36 | Br | Cl | thiazolidinyl (H S) | 187–189 | 197–198 (decomp.) |

-continued

| Example No. | $R_1$ | $R_2$ | $R_3$ | M.P. °C. | M.P. of corresponding hydrazide of the formula VII, °C. |
| --- | --- | --- | --- | --- | --- |
| 37 | Br | Cl | 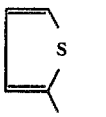 | 231–233 | 215–218 (decomp.) |
| 38 | Br | Cl | 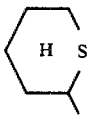 | 209–211 | 213 (decomp.) |
| 39 | Br | Cl | 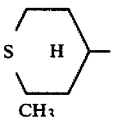 | 260–261 | 204–206 |
| 40 | H | Cl | 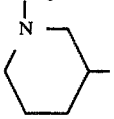 | 98–100 | 155 (decomp.) |
| 41 | $C_2H_5$ | Cl | 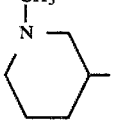 | 120–122 | 165–168 (decomp.) |
| 42 | Br | Br | 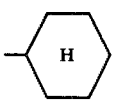 | 190–191 | 220 (decomp.) |
| 43 | Br | Br | 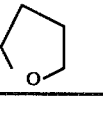 | 140–141 | 172 (decomp.) |

The compounds of this invention, that is, those embraced by formula I above and their non-toxic, pharmacologically acceptable acid addition salts, have useful pharmacodynamic properties. More particularly, they exhibit anxiety-relieving (anxiolytic), tension-relieving, muscle-relaxing and very effective anticonvulsive activities in warm-blooded animals, such as mice and rats. They also increase the food-intake in mammals. The compounds of this invention, moreover, are characterized by extraordinarily low toxicity.

In the so-called pentetrazole-antagonism test for anticonvulsive activity the compounds of the present invention have been found to be far superior to the thieno-1,4-diazepines disclosed in German Offenlegungsschrift Nos. 2,155,403 and 2,221,623; and while the compounds of this invention exhibit an activity picture similar to that of the 8-alkyl-6-aryl-thieno-[2,3e]-4H-s-triazolo-[3,4c]-1,4-diazepines disclosed in German Offenlegungsschrift No. 2,229,845, the former's intensity of activity is more than ten times that of the latter's.

Particularly effective are those compounds of the formula I wherein $R_1$ is bromine, $R_2$ is chlorine or bromine, and $R_3$ is cycloalkyl, tetrahydropyranyl, tetrahydrothiopyranyl, bromine or optionally substituted piperidyl, and their non-toxic acid addition salts. The following are specific examples of such particularly effective compounds:

8-bromo-6-o-chloro-phenyl-1-cyclohexyl-4H-s-triazolo-[3,4c]-thieno-[2,3e]-1,4-diazepine ($R_1$=Br, $R_2$=Cl, $R_3$=$C_6H_{11}$);

8-bromo-6-o-bromo-phenyl-1-cyclohexyl-4H-s-triazolo-[3,4c]-thieno-[2,3e]-1,4-diazepine ($R_1$=Br, $R_2$=Br, $R_3$=$C_6H_{11}$);

8-bromo-6-o-chloro-phenyl-1-cyclobutyl-4H-s-triazolo-[3,4c]-thieno-[2,3e]-1,4-diazepine ($R_1$=Br, $R_2$=Cl, $R_3$=$C_4H_7$);

8-bromo-6-o-chloro-phenyl-1-cyclopentyl-4H-s-triazolo-[3,4c]-thieno-[2,3e]-1,4-diazepine ($R_1$=Br, $R_2$=Cl, $R_3$=$C_5H_9$);

8-bromo-6-o-chloro-phenyl-1-cyclopropyl-4H-s-triazolo-[3,4c]-thieno-[2,3e]-1,4-diazepine ($R_1$=Br, $R_2$=Cl, $R_3$=$C_3H_5$);

8-bromo-6-chloro-phenyl-1-tetrahydropyranyl-(4)-4H-s-triazolo-[3,4c]-thieno-[2,3e]-1,4-diazepine ($R_1$=Br, $R_2$=Cl, $R_3$=$C_5H_{10}O$);

8-bromo-6-o-chloro-phenyl-1-tetrahydropyranyl-(3)-4H-s-triazolo[3,4c]-thieno-[2,3]-1,4-diazepine ($R_1$=Br, $R_2$=Cl, $R_3$=$C_5H_{10}O$);

8-bromo-6-o-chloro-phenyl-1-tetrahydrofuranyl-(2)-4H-s-triazolo-[3,4c]-thieno-[2,3e]-1,4-diazepine ($R_1$=Br, $R_2$=Cl, $R_3$=$C_4H_7O$);

8-bromo-6-o-bromo-phenyl-1-tetrahydrofuranyl-(2)-4H-s-triazolo-[3,4c]-thieno-[2,3e]-1,4-diazepine ($R_1$=Br, $R_2$=Br, $R_3$=$C_4H_7O$);

8-bromo-6-o-chloro-phenyl-1-[N-methylpiperidyl-(3)]-4H-s-triazolo-[3,4c]-thieno-[2,3e]-1,4-diazepine ($R_1=Br$, $R_2=Cl$, $R_3=CH_3-N-C_5H_{10}$);

8-bromo-6-o-chloro-phenyl-1-tetrahydrothiopyranyl-(2)-4H-s-triazolo-[3,4c]-thieno-[2,3e]-1,4-diazepine ($R_1=Br$, $R_2=Cl$, $R_3=C_5H_{10}S$);

1,8-dibromo-6-o-chloro-phenyl-4H-s-triazolo-[3,4c[-thieno[2,3e]-1,4-diazepine ($R_1=Br$, $R_2=Br$); and 8-bromo-6-o-chloro-phenyl-1-methoxy-4H-s-triazolo-[3,4c]-thieno-[2,3e]-1,4-diazepine ($R_1=Br$, $R_2=Cl$, $R_3=OCH_3$)

and their acid addition salts.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0083 to 0.84 mgm/kg body weight, preferably 0.016 to 0.42 mgm/kg body weight (oral). The daily dose rate is 0.083 to 2.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 44

Tablets

The tablet composition is compounded from the following ingredients:

| | | |
|---|---|---|
| 8-Bromo-6-(o-chloro-phenyl)-1-cyclohexyl -4H-s-triazolo-[3,4c]-thieno-[2,3e]- 1,4-diazepine | 0.5 | parts |
| Lactose | 50.0 | parts |
| Corn starch | 43.5 | parts |
| Soluble starch | 5.0 | parts |
| Magnesium stearate | 1.0 | parts |
| Total | 100.0 | parts |

Preparation:

The triazolo-thieno-diazepine compound and the magnesium stearate are admixed with each other, the mixture is moistened with an aqueous solution of the soluble starch, the moist mass is granulated through a 1 mm-mesh screen, the granulate is dried and again passed through the screen, and the dry granulate is intimately admixed with the lactose and the corn starch. The resulting composition is compressed into 100 mgm/tablets, each of which contains 0.5 mgm of the triazolo-thieno-diazepine compound and is an oral dosage unit composition with effective anxiolytic, tension-relieving, muscle-relaxing and anticonvulsive action.

EXAMPLE 45

Coated pills

The pill core composition is compounded from the following ingredients:

| | | |
|---|---|---|
| 8-Bromo-6-(o-bromo-phenyl)-1-cyclohexyl -4H-s-triazolo-[3,4c]-thieno-[2,3e]- 1,4-diazepine | 1.0 | parts |
| Lactose | 28.5 | parts |
| Corn starch | 19.0 | parts |
| Gelatin | 1.0 | parts |
| Magnesium stearate | 0.5 | parts |
| Total | 50.0 | parts |

Preparation:

The triazolo-thieno-diazepine compound, the lactose and the corn starch are intimately admixed with each other, the mixture is granulated through a 1 mm-mesh screen with the aid of an aqueous 10% solution of the gelatin, the granulate is dried and again passed through the screen, and the dry granulate is admixed with the magnesium stearate. The resulting composition is compressed into 50 mgm-pill cores which are subsequently coated with a thin shell consisting essentially of a mixture of sugar, titanium dioxide, talcum and gum arabic, and finally polished with beeswax. Each coated pill contains 1 mgm of the triazolo-thieno-diazepine compound and is an oral dosage unit composition with effective anxiolytic, tension-relieving, muscle-relaxing and anticonvulsive action.

EXAMPLE 46

Suppositories

The suppository composition is compounded from the following ingredients:

| | | |
|---|---|---|
| 8-Bromo-6-(o-chloro-phenyl)-1-cyclobutyl -4H-s-triazolo-[3,4c]-thieno-[2,3e]- 1,4-diazepine | 5.0 | parts |
| Suppository base (e.g. cocoa butter) | 1695.0 | parts |
| Total | 1700.0 | parts |

Preparation

The suppository base is melted and cooled to 40° C., the finely pulverized triazolo-thieno-diazepine compound is stirred into the suppository base with the aid of an immersion homogenizer, and 1700 mgm-portions of the resulting mixture at 35° C. are poured into cooled suppository molds and allowed to harden therein. Each suppository contains 5 mgm of the thiazolo-thieno-diazepine compound and is a rectal dosage unit composition with effective anxiolytic, tension-relieving, muscle-relaxing and anticonvulsive action.

Analogous results are obtained when any one of the other triazolo-benzodiazepinones embraced by formula I or a non-toxic, pharmacologically acceptable acid addition salt thereof was substituted for the particular triazolo-thienodiazepine in Examples 44 through 46. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

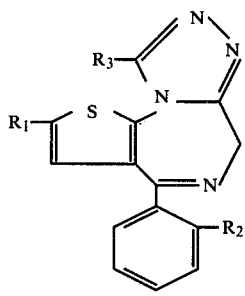

wherein
R₁ is bromine;
R₂ is chlorine or bromine; and
R₃ is tetrahydrofuranyl, tetrahydropyranyl, N-methyl-piperidyl, or tetrahydrothiopyranyl;
or when R₃ is other than tetrahydrothiopyranyl a non-toxic, pharmacologically acceptable acid addition salt thereof.

2. A compound of claim 1,
where
R₁ is bromine,
R₂ is chlorine or bromine, and
R₃ is tetrahydropyranyl, tetrahydrothiopyranyl or N-methyl-piperidyl,
or when R₃ is other than tetrahydrothiopyranyl, a non-toxic, pharmacologically acceptable acid addition salt thereof.

3. A compound of claim 2, which is 8-bromo-6-(o-chloro-phenyl)-1-tetrahydrofuranyl-(2)-4H-s-triazolo-[3,4c]-thieno[2,3e]-1,4-diazepine or a non-toxic, pharmacologically accpetable acid addition salt thereof.

4. A compound of claim 2, which is 8-bromo-6-(o-bromo-phenyl)-1-tetrahydrofuranyl-(2)-4H-s-triazolo-[3,4c]-thieno-[2,3e]-1,4-diazepine or a non-toxic, pharmacologically acceptable acid addition salt thereof.

5. A compound of claim 2, which is 8-bromo-6-(o-chloro-phenyl)-1-tetrahydropyranyl-(4)-4H-s-triazolo-[3,4c]-thieno-[2,3e]-1,4-diazepine or a non-toxic, pharmacologically acceptable acid addition salt thereof.

6. A compound of claim 2, which is 8-bromo-6-(o-chloro-phenyl)-1-tetrahydropyranyl-(3)-4H-s-triazolo-[3,4c]thieno-[2,3e]-1,4-diazepine or a non-toxic, pharmacologically acceptable acid addition salt thereof.

7. A compound of claim 2, which is 8-bromo-6-(o-bromo-phenyl)-tetrahydropyranyl-(4)-4H-s-triazolo-[3,4c]-thieno-[2,3e]-1,4-diazepine or a non-toxic, pharmacologically acceptable acid addition salt thereof.

8. A compound of claim 2, which is 8-bromo-6-(o-chloro-phenyl)-1-[N-methyl-piperidyl-(3)]-4H-s-triazolo-[3,4c]-thieno-[2,3e]-1,4-diazepine or a non-toxic, pharmacologically acceptable acid addition salt thereof.

9. The compound of claim 2, which is 8-bromo-6-(o-chloro-phenyl)-1-tetrahydrothiopyranyl-(2)-4H-s-triazolo-[3,4c]-thieno-[2,3e]-1,4-diazepine.

10. The compound of claim 2, which is 8-bromo-6-(o-chloro-phenyl)-1-tetrahydrothiopyranyl-(4)-4H-s-triazolo-[3,4c]-thieno-[2,3e]-1,4-diazepine.

11. A pharmaceutical dosage unit composition consisting essentially of an inert pharmaceutical carrier and an effective anxiolytic, tension-relieving, muscle-relaxing or anticonvulsive amount of a compound of claim 1.

12. The method of relieving anxiety, relieving tension, relaxing the muscles or suppressing convulsions in a warm-blooded animal, which comprises perorally, parenterally or rectally administering to said animal an effective anxiolytic, tension-relieving, muscle-relaxing or anticonvulsive amount of a compound of claim 1.

* * * * *

UNITED STATES PATENT AND TRADEMARK OFFICE
CERTIFICATE OF CORRECTION

PATENT NO. : 4,199,588
DATED : April 22, 1980
INVENTOR(S) : KARL-HEINZ WEBER ET AL.

It is certified that error appears in the above-identified patent and that said Letters Patent are hereby corrected as shown below:

Column 1, line 40: "substitutable nitrogen nitrogen"

should read -- substitutable nitrogen --.

Column 11, line 8: "3H)-" should read -- 3H- --.

Column 16, line 56: "8-bromo-6-chloro" should read

-- 8-bromo-6-o-chloro --.

Signed and Sealed this

Twenty-eighth Day of October 1980

[SEAL]

Attest:

SIDNEY A. DIAMOND

Attesting Officer

Commissioner of Patents and Trademarks